US00PP13877P29

(12) United States Plant Patent
Warner

(10) Patent No.: US PP13,877 P2
(45) Date of Patent: Jun. 10, 2003

(54) ROSA PLANT NAMED 'CHEWPEARL'

(76) Inventor: Christopher Warner, Greenfields Brockton, Newport, Shropshire (GB), TF10 9EP ( * ) Notice: Subject to any disclaimer, the term of this patent is extended or adjusted under 35 U.S.C. 154(b) by 0 days.

(21) Appl. No.: 10/041,816

(22) Filed: Jan. 7, 2002

(51) Int. Cl.[7] ..... A01H 5/00
(52) U.S. Cl. ..... Plt./107
(58) Field of Search ..... Plt./114, 109, 107, Plt./102

(56) References Cited

U.S. PATENT DOCUMENTS

PP9,012 P * 12/1994 Warner

* cited by examiner

*Primary Examiner*—Bruce R. Campell
*Assistant Examiner*—June Hwu

(57) ABSTRACT

A new cultivar of Rosa plant named 'Chewpearl' that is characterized by upright, columnar growth habit, small glossy, dark green leaves, small satin-pink flowers and a long blooming period. In combination these traits set 'Chewpearl' apart from all other existing varieties of Rosa known to the inventor.

2 Drawing Sheets

Genus: Rosa.
Species: ×hybrida.
Denomination: 'Chewpearl'.

BACKGROUND OF THE INVENTION

The present invention relates to a new and distinct cultivar of rose plant botanically known as Rosa and hereinafter referred to by the cultivar name 'Chewpearl'.

The new cultivar is the product of a breeding program begun in 1982 by the inventor in a cultivated area of Shropshire, England. The breeding program is aimed at developing a new class of disease resistant patio and upright, columnar rose plants with a wide range of flower colors.

'Chewpearl' is a hybrid seedling that originated from the induced hybridization of the female or seed parent Rosa 'LAURA FORD' [CHEWARVEL] (U.S. Plant Pat. No. 9,012) and the male or pollen parent Rosa 'Congratulations' [KORLIFT] (unpatented). The new cultivar 'Chewpearl' was selected by the inventor in 1992 as a plant within the progeny of the stated cross in a controlled environment of Shropshire, England. 'Chewpearl' is an upright, columnar rose with small dense, dark green leaves and small fragrant satin-pink colored flowers, that contrast brightly against the dark foliage. The recipient of the Bronze Award in the 2001 Buenos Aires Rose Trials, 'Chewpearl' is consistently free flowering, forming a continuous column of color from late spring to early winter.

The closest comparison plant is Rosa 'LAURA FORD' which exhibits yellow flowers. 'Chewpearl' is distinguishable from 'LAURA FORD' by flower color and darker green foliage. 'Chewpearl' differs from the male parent 'Congratulations' in height and size of flowers. 'Congratulations' is taller in height and exhibits large flowers.

Asexual reproduction was accomplished by the inventor in Shropshire, England in 1992 using softwood cuttings. Since that time, under careful observation, the unique characteristics of the new rose cultivar have been uniform, stable and reproduced true to type in successive generations of asexual reproduction. In addition to softwood cuttings 'Chewpearl' can be asexually propagated using micro propagation and budding.

SUMMARY OF THE INVENTION

The following represent the distinguishing characteristics of the new Rosa cultivar 'Chewpearl'. These traits in combination distinguish 'Chewpearl' as a new and distinct cultivar apart from all other existing varieties of Rosa known to the inventor. 'Chewpearl' has not been tested under all possible conditions and phenotypic differences may be observed with variations in environmental, climatic, and cultural conditions, however, without any variance in genotype.

1. Rosa 'Chewpearl' exhibits small satin-pink flowers
2. Rosa 'Chewpearl' exhibits an upright, columnar growth habit.
3. Rosa 'Chewpearl' is free flowering, blooming from late spring until the first frost.
4. An individual flower exhibited on Rosa 'Chewpearl' lasts 6–10 days on the plant.
5. Rosa 'Chewpearl' exhibits small glossy, dark green leaves.
6. Rosa 'Chewpearl' roots well from cuttings, micro propagation and budding.
7. Rosa 'Chewpearl' is hardy to minus 12° Centigrade.

BRIEF DESCRIPTION OF THE DRAWINGS

The accompanying color drawings illustrate the overall appearance of the new plant variety of Rosa named 'Chewpearl' showing the colors as true as it is reasonably possible to obtain in colored reproductions of this type. Colors in the drawings may differ from the color values cited in the detailed botanical description which more accurately describe the actual colors of the new variety 'Chewpearl'.

The plants illustrated on sheet 1 are three-year-old budded rose plants field grown in Shropshire, England.

The drawing on sheet 1 illustrates the entire plants in full bloom.

The drawing on sheet 2 is a close-up view of the flowers on an 8-month-old plant in a 1-liter container. The drawings were made using conventional techniques and although colors may appear different from actual colors due to light reflectance, they are as accurate as possible by conventional photography.

BOTANICAL DESCRIPTION OF THE PLANT

The following is a detailed description of the new Rosa cultivar named 'Chewpearl'. Data was collected from 4-inch container plants and 1-liter container plants grown indoors in Arroyo Grande, Calif. The color determinations are in accordance with The 2001 Royal Horticultural Society Colour Chart of The Royal Horticulatural Society, London, England, except where general color terms of ordinary dictionary significance are used. Growing requirements are similar to the species.

Botanical classification: Rosa 'Chewpearl'.
Species: ×hybrida.
Commercial classification: Shrub.
Common name: Rose.
Recommended container size: 1-liter.
Type: Perennial.
Use: Garden border, Container.
Parentage: 'Chewpearl' is a hybrid plant that resulted from the induced hybridization of the following parent plants:
*Female parent.*—Rosa 'LAURA FORD' [CHEWARVEL] (U.S. Plant Pat. No. 9,012).
*Male parent.*—Rosa 'Congratulations' [KORLIFT] (unpatented).
Vigor: Very Vigorous.
Growth habit: Upright and columnar.
Plant shape: Rectangular to columnar.
Height (at maturity): 2.5 meters in height at maturity.
Width (at maturity): 1 meter in width at maturity.
Hardiness: Hardy to minus 12° Centigrade.
Propagation: Cuttings, micro propagation and budding.
Time to initiate roots: Approximately 21 days are required to produce roots on an initial cutting.
Crop time: Approximately 8 months are needed to achieve a finished 1-liter plant in flower from an un-rooted cutting.
Root system: Fibrous.
Light: Plant in full sun.
Soil: Plant in moist but well drained soil.
Seasonal interest: Satin-pink flowers from late spring to first frost.
Disease and pest resistance/susceptibility: None observed to date.
Stem:
*Branching habit.*—Basal.
*Stem strength.*—Strong and pliable.
*Mature stem color.*—N77A.
*Immature stem color.*—Colors N77A and 144A are both present on an individual stem.
*Anthocyanic coloring* (*stem*).—None observed to date.
*Immature stem shape.*—Cylindrical.
*Mature stem dimensions.*—20–62 cm. in length and 4 mm. in width.
*Immature stem dimensions.*—6 cm. in length and 2 mm. in width.
*Mature stem shape.*—Cylindrical.
*Immature stem surface.*—Glabrous.
*Mature stem surface.*—Rugose.
*Internode length.*—1.50 cm. between nodes.
*Quantity of thorns* (*immature and mature*).—Small amount.
*Immature thorn dimensions.*—3–5 mm. in length and 0.50 mm. in width and base near stem is 1.50 mm.
*Immature thorn shape.*—Slightly curved.
*Immature thorn color.*—Thorns that are 144A and thorns that are 182C are both present on an individual stem.
*Mature thorn shape.*—Curved.
*Mature thorn dimensions.*—1.5 cm. in length and 0.50 cm. in width.
*Mature thorn color.*—198D.
Foliage:
*Type.*—Deciduous.
*Arrangement.*—Alternate.
*Leaf shape.*—Oval.
*Vein pattern.*—Pinnate.
*Vein color* (*adaxial and abaxial surfaces*).—N77A.
*Leaf margins.*—Serrate.
*Leaf division.*—Simple.
*Appearance.*—Glossy.
*Mature leaf color* (*adaxial surface*).—Closest to 131A.
*Mature leaf color* (*abaxial surface*).—137B.
*Immature leaf color* (*abaxial surface*).—Surface color is 144A and margins are 185A.
*Immature leaf color* (*adaxial surface*).—Surface color is 137B and margins are 185A.
*Anthocyanic coloring* (*leaves*).—None observed to date.
*Mature and immature leaf surfaces* (*adaxial surface*).—Glabrous.
*Mature and immature leaf surfaces* (*abaxial surface*).—Slightly pubescent.
*Stipule color* (*immature*).—137B with edges that are 185A.
*Stipule color* (*mature*).—185A.
*Stipule dimensions* (*immature*).—0.25 cm. in length and 0.25 cm. in width.
*Stipule dimensions* (*mature*).—1.50 cm. in length and 0.50 cm. in width.
*Mature leaf dimensions.*—Mature leaves are an average of 2.50 cm. in width and 2.50–3.50 cm. in length.
*Immature leaf dimensions.*—Immature leaves are an average of 1 cm. in width and 2 cm. in length.
*Leaf apex.*—Acuminate.
*Leaf base.*—Rounded.
*Leaf attachment.*—Petiolate.
*Petiole shape.*—Sulcate.
*Petiole dimensions.*—9 mm. in length and less than 0.50 mm. in width.
*Petiole color* (*immature*).—Colors 144A and 183A are both individually present on immature petioles.
*Petiole color* (*mature*).—N77A.
*Petiole surface.*—Pubescent.
Flower:
*Number of flowers per flowering stem.*—3–5.
*Flower arrangement.*—Corymb.
*Flower type.*—Double.
*Flowering habit.*—Continuous.
*Flowering season.*—Late spring to first frost.
*Lastingness of flower.*—Individual flower lasts 6–10 days on plant.
*Fragrance.*—Moderately sweet fragrance.
*Flower bud dimensions* (*sepals closed*).—Average of 1.50–1.75 cm. in length and 1.50–1.75 cm. in width.
*Flower bud shape.*—Obovate.
*Bud color* (*when sepals have divided*).—52B.
*Petal color* (*adaxial surfaces*).—Closest to 49D when flower is fully opened.
*Petal color* (*abaxial surfaces*).—Closest to 49D when flower is fully opened.

*Basal spot color* (*adaxial surfaces*).—11D.
*Basal spot color* (*abaxial surfaces*).—11D.
*Petal color of adaxial surfaces* (*when flower is opening*).—49A.
*Petal color of abaxial surfaces* (*when flower is opening*).—49A.
*Petal surfaces* (*adaxial and abaxial*).—Lustrous.
*Petal margins.*—Entire.
*Petal apex.*—Obtuse.
*Petal base.*—Acute.
*Petal shape.*—Closest to Obdeltoid.
*Petal dimensions.*—Average of 2.50 cm. in width and 2.50 cm. in length.
*Petals fused or unfused.*—Unfused.
*Petal texture.*—Firm and glabrous.
*Number of petals.*—20–50 in number.
*Flower dimensions.*—4 cm. in diameter and 1.50–2 cm. in depth.
*Aspect.*—Facing upward and outward.
*Self-cleaning or persistent.*—Self-cleaning.
*Peduncle dimensions.*—5 cm. in length and 2 mm. in width.
*Peduncle color.*—N77A.
*Anthocyanic coloring* (*peduncle*).—None observed to date.
*Peduncle surface.*—Rugose.
*Peduncle shape.*—Cylindrical.
*Sepals.*—Five in number.
*Sepal shape.*—Gladiate.
*Sepal margin.*—Entire.
*Sepal dimensions.*—0.75 cm. in width and 1.75 cm. in length.
*Sepal color* (*adaxial surfaces*).—Colors range from both 144A and N77A present on an individual sepal when tightly closed, to both 128C and 128D present on an individual sepal when fully open.
*Sepal color* (*abaxial surface*).—Colors range from both 144A and N77A present when tightly closed to 128C and 128D when fully open.
*Anthocyanic coloring* (*sepals*).—None observed to date.
*Sepal surfaces* (*adaxial and abaxial surfaces*).—Pubescent.
*Sepal apex.*—Cirrose.
*Sepal base.*—Truncate.

Reproductive organs:
*Stamen.*—40–100 in whorl.
*Stamen shape.*—Filament.
*Stamen color.*—49D.
*Stamen dimensions.*—8 mm. in length and less than 0.50 mm. in width.
*Anther dimensions.*—1 mm. in length and 0.75 mm. in width.
*Anther shape.*—Oval.
*Anther color.*—165B.
*Pollen color.*—165B.
*Amount of pollen.*—Moderate amount.
*Pistil.*—One made up of 10–15 united filaments.
*Pistil dimensions.*—7 mm. in length and 3 mm. in width.
*Pistil color.*—N34A.
*Pistil shape.*—Columnar.
*Style dimensions.*—6 mm. in length and 3 mm. in width.
*Style color.*—N34A.
*Style.*—10–15 free filaments united at base into one column.
*Style shape.*—Columnar.
*Stigma.*—10–15.
*Stigma shape.*—Oval.
*Stigma color.*—N34A.
*Stigma dimensions.*—Together the stigmas are 4 mm. in diameter and 0.75 mm. in length. Individually each is less than 0.50 mm. in diameter.
*Ovary position.*—Inferior.
*Ovary color.*—144C.
*Ovary.*—Many in number.
*Ovary dimensions.*—Less than 1.50 mm. in length and less than 0.50 mm. in diameter.
*Ovary shape.*—Oval.
*Receptacle shape.*—Closest to globular.
*Receptacle surface.*—Pubescent.
*Receptacle color.*—144A.
*Receptacle dimensions.*—0.75 cm. in length and 1 cm. in width.

Seed production:
*Quantity of seed.*—50–100 or more in number.
*Shape of seed.*—Closest to rectangular in shape.
*Color of seed.*—Both colors 199D and 200A are present on each individual seed.
*Dimensions of seed.*—1 mm. in length and 0.75 mm. in width.
*Hip dimensions.*—19 mm in length and 18 mm in width.
*Shape of hip.*—Closest to globular.
*Hip surface.*—Pubescent.
*Hip color.*—200A.

I claim:

1. A new and distinct variety of Rosa plant named 'Chewpearl', as described and illustrated.

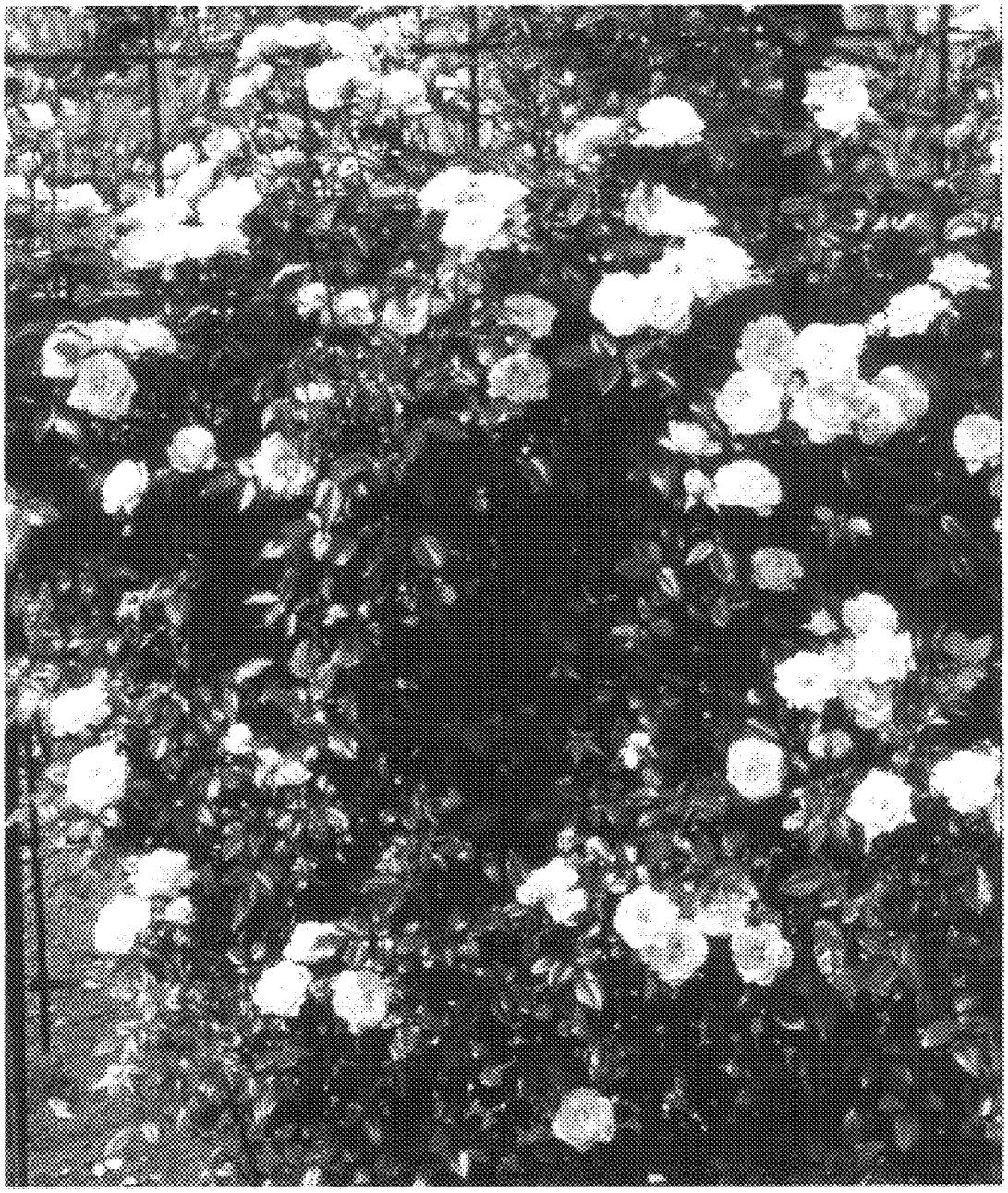

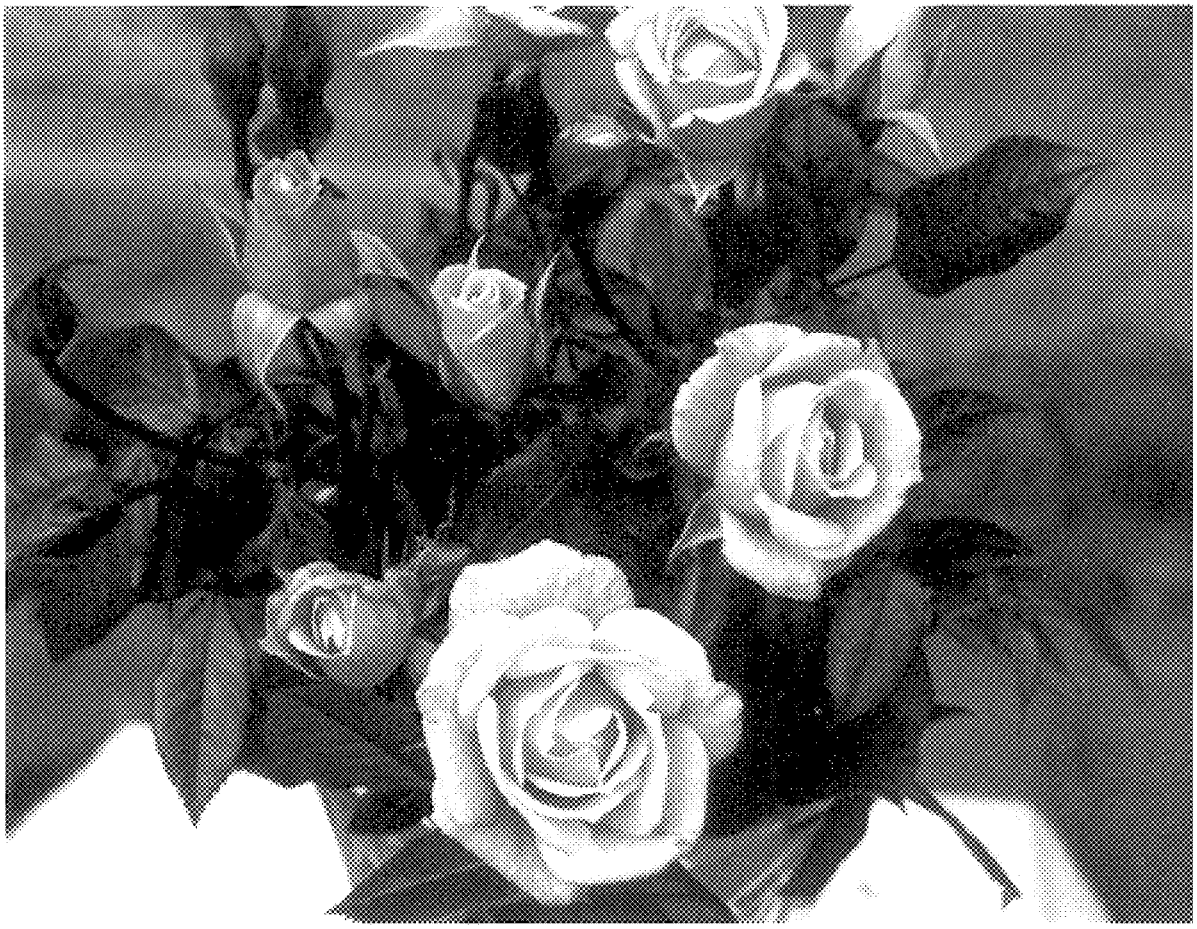

* * * * *